US00PP35976P2

(12) United States Plant Patent
Castañeda Solares

(10) Patent No.: US PP35,976 P2
(45) Date of Patent: Jul. 9, 2024

(54) BLACKBERRY PLANT NAMED 'MEF-2022.1'

(50) Latin Name: ***Rubus* L. subg. *Rubus*.**
Varietal Denomination: MEF-2022.1

(71) Applicant: Pure Fresh LLC, Dania Beach, FL (US)

(72) Inventor: Roberto Castañeda Solares, Guatemala (GT)

(73) Assignee: Pure Fresh LLC, Pompano Beach, FL (US)

( * ) Notice: Subject to any disclaimer, the term of this patent is extended or adjusted under 35 U.S.C. 154(b) by 0 days.

(21) Appl. No.: 17/803,981

(22) Filed: Feb. 15, 2023

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 5/0887
See application file for complete search history.

*Primary Examiner* — Kent L Bell
(74) *Attorney, Agent, or Firm* — Hunt IP Law

(57) ABSTRACT

A new and distinct variety of blackberry plant 'MEF-2022.1' is provided. The variety can be distinguished by its outstanding features of thornless stems, strong canes, large and long shaped fruit, vigor, high fruit yields, easily harvested fruit, long shelf life, and high tolerance to common blackberry diseases.

9 Drawing Sheets

Latin name of the genus and species:
Genus—*Rubus*.
Subgenus—*Rubus* L. subg. *Rubus*.
Variety denomination: The new *Rubus* plant claimed is of the variety denominated 'MEF-2022.1'.

CROSS REFERENCE TO RELATED APPLICATIONS

None.

BACKGROUND OF THE INVENTION

The present invention relates to a new and distinct annual variety of blackberry, which has been given the variety denomination of 'MEF-2022.1'. 'MEF-2022.1' is intended for use as commercial variety intended for the fresh fruit market.

The new blackberry plant is a product of a planned breeding program conducted in Chimaltenango Guatemala. The objective of the breeding program was to develop a new blackberry plant with good fruit quality, productivity, and good shelf life.

SUMMARY OF THE INVENTION

The present invention relates to a new and distinct annual variety of blackberry, which has been given the variety denomination of 'MEF-2022.1'. 'MEF-2022.1' is intended for use as a commercial variety intended for the fresh fruit market.

The new blackberry variety originated from a cross-pollination of two unidentified proprietary selections of *Rubus* in 2015. Seed was collected from a few potential parent plants, combined and sown. The variety was discovered and selected as a single plant in a controlled environment in Chimaltenango Guatemala in January 2016.

Selection criteria included thornless stems, strong canes, large and long shaped fruit, vigor, high fruit yields, easily harvested fruit, long shelf life, and high tolerance to common blackberry diseases.

The selection was subsequently evaluated for 3 years at cultivation fields in Sacatepéquez and Chimaltenango Guatemala.

Asexual reproduction of the new variety by rooting adventitious shoots from root cuttings since 2019 in Chimaltenango Guatemala has demonstrated that the new variety reproduces true to type with all of the characteristics, as herein described, firmly fixed and retained through successive generations of such asexual propagation.

The following characteristics of the new variety have been repeatedly observed and can be used to distinguish 'MEF-2022.1' as a new and distinct variety of blackberry plant:

1. Thornless stems
2. Strong canes
3. Large/long fruit
4. Vigorous plants
5. High fruit yields
6. Easy to harvest fruit
7. Sweet fruit taste Plants of the new Blackberry can be compared to plants of *Rubus* 'APF-45' (U.S. Plant Pat. No. 22,449 P3) and 'APF-122' (U.S. Plant Pat. No. 27,401 P3) and differ in the following characteristics.

a. Plants of 'MEF-2022.1' have thornless stems, while 'APF45' and 'APF 122' have thorned stems.
b. Fruits of the new variety are larger (13 to 16 grams per fruit) than 'APF45' (8 to 10 grams per fruit) and 'APF122' (6 to 8 grams per fruit).
c. Plants of the variety are more vigorous than 'APF45' and 'APF122'.

d. 'MEF-2022.1' is later in production (average 7 months) 'APF-122' (average 5 months) and 'APF-45' (average 6 months) as seen in Guatemala.

BRIEF DESCRIPTION OF THE DRAWINGS

The accompanying photographic illustrations show the typical appearance of the new plant 'MEF-2022.1'. The colors are as nearly true as is reasonably possible in a color representation of this type. Colors in the photographs may differ slightly from the color values cited in the detailed botanical description which accurately describe the colors of the new plant.

DETAILED BOTANICAL DESCRIPTION

Figure 1:
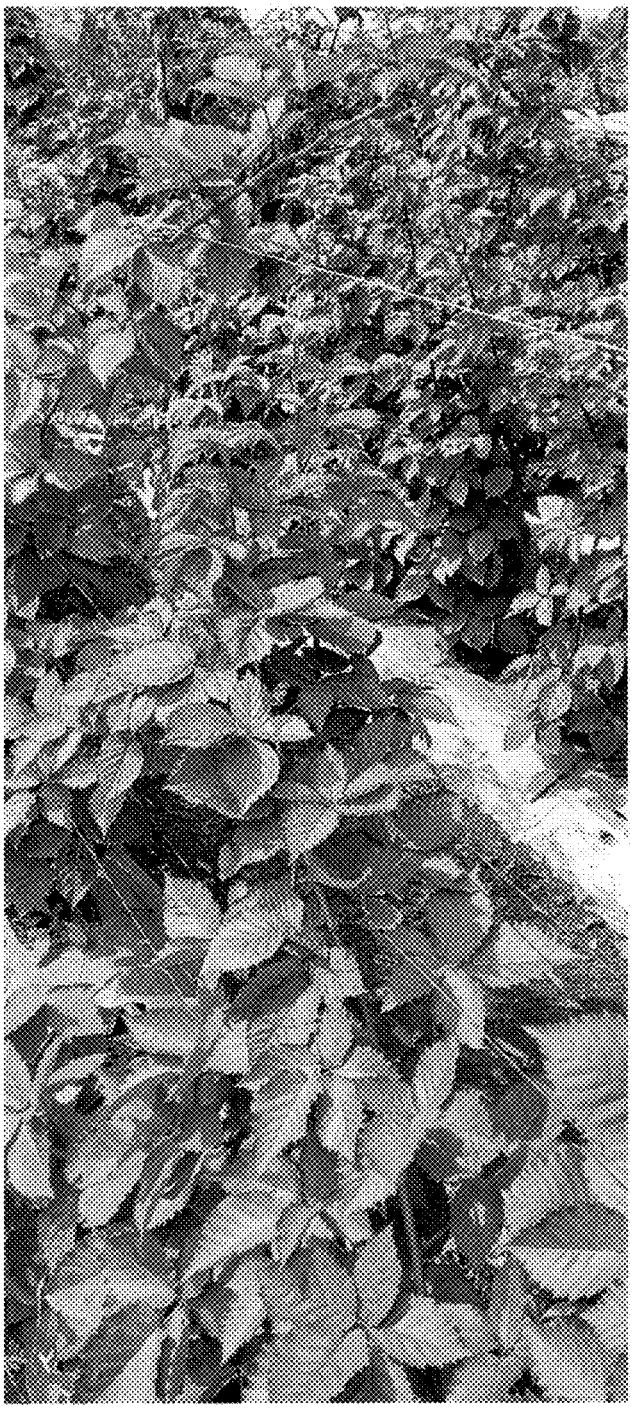
FIG. 1 is a photograph of the new plant 'MEF-2022.1', demonstrating growing cane.
Figure 2:
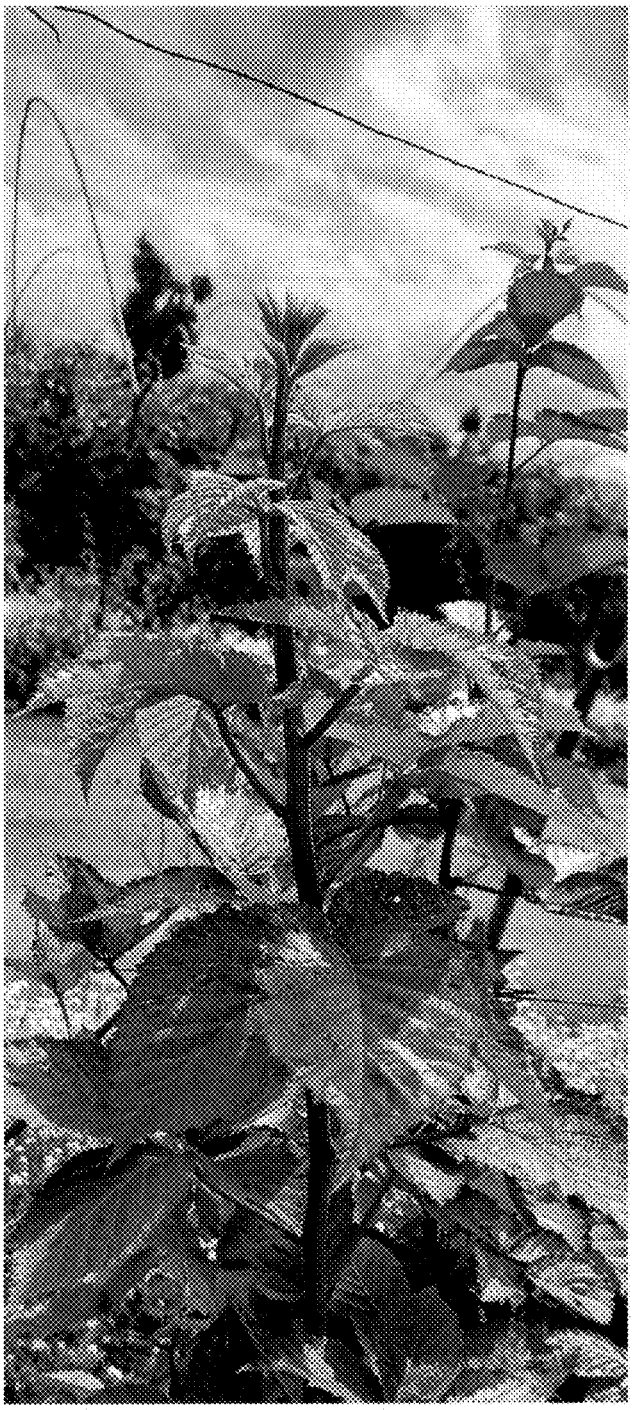
FIG. 2 Is a photograph of the new plant 'MEF-2022.1', demonstrating growing cane.
Figure 3:
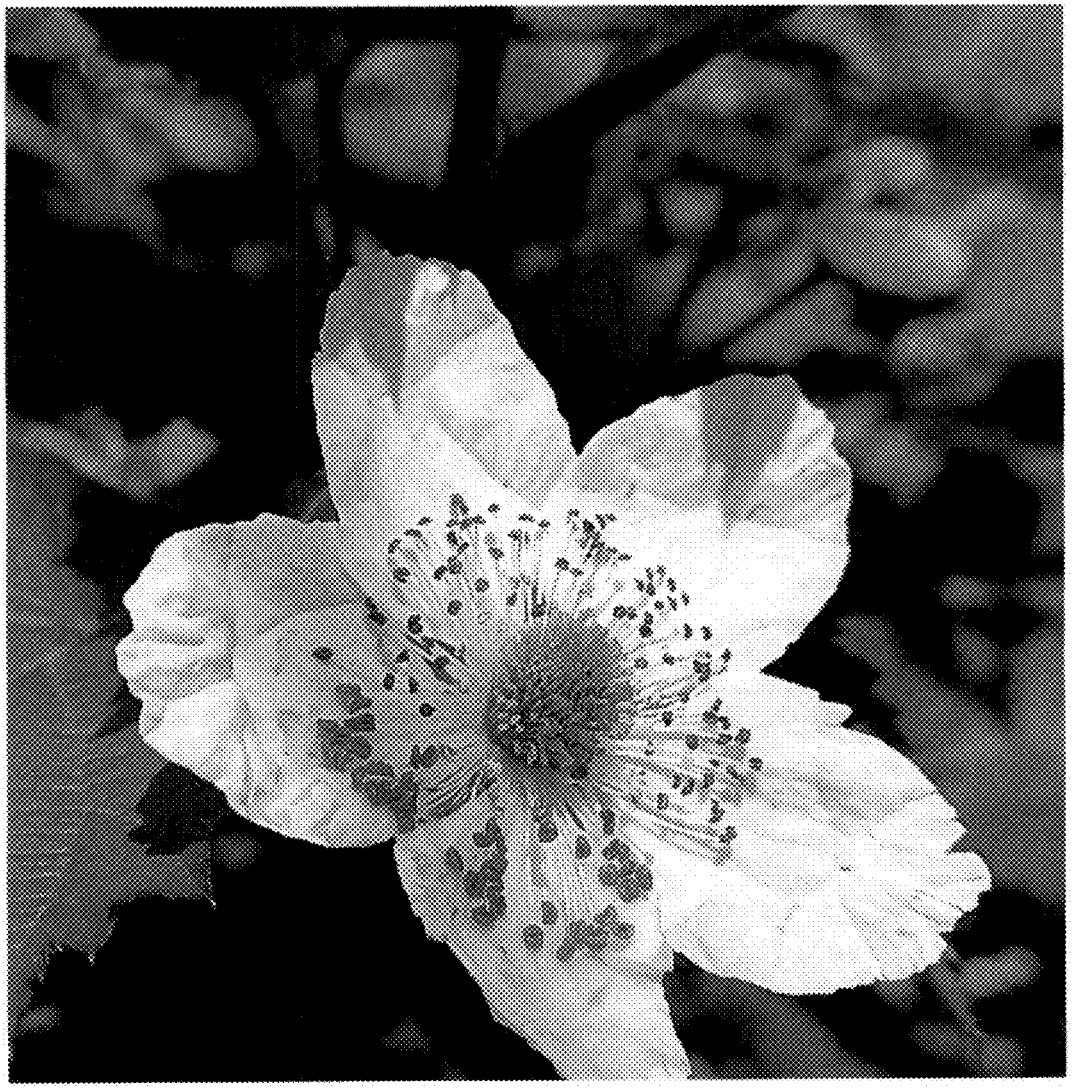
FIG. 3 is a photograph of a flower of the new plant 'MEF-2022.1' at 7 months.
Figure 4:
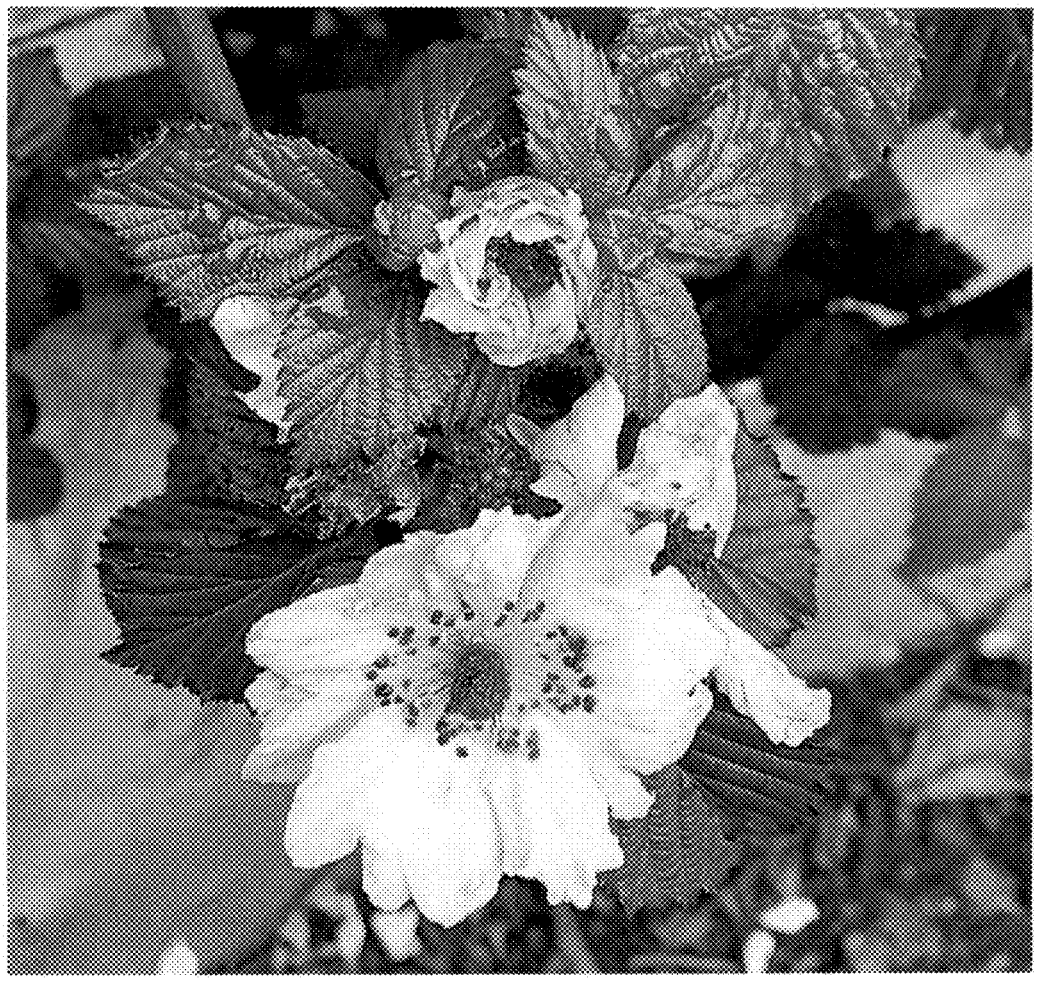
FIG. 4 is a photograph of flowers of the new plant 'MEF-2022.1' at 7 months.
Figure 5:
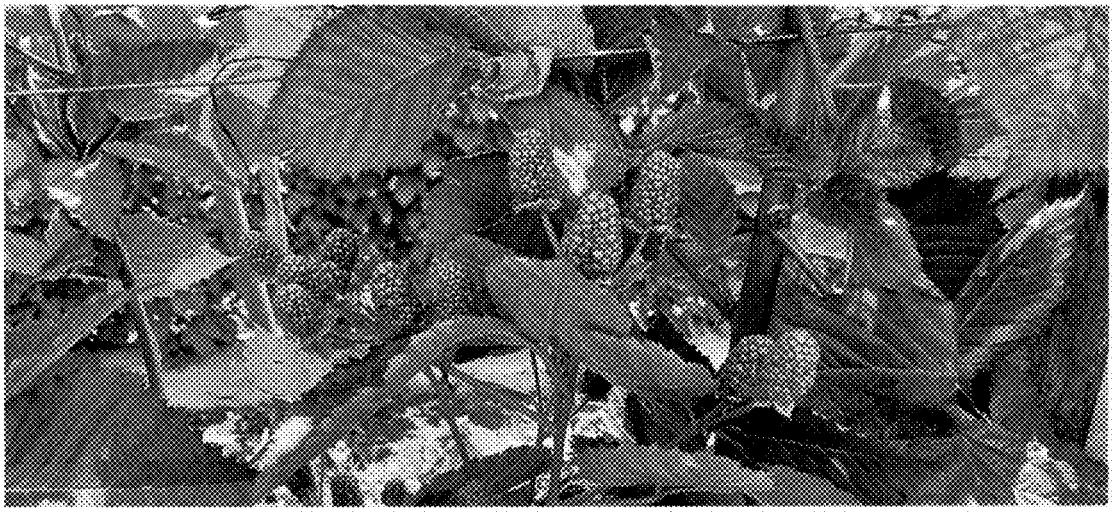
FIG. 5 is a photograph of ripe fruits of the new plant 'MEF-2022.1' at 7 months.
Figure 6:
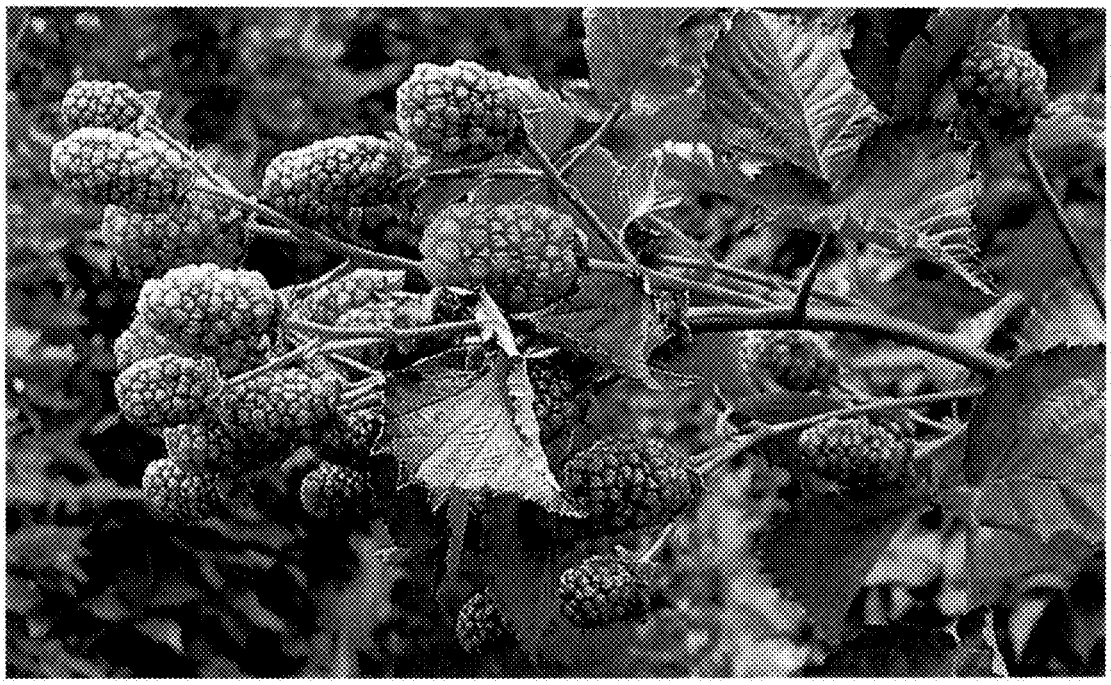
FIG. 6 is a photograph of unripe fruits of the new plant 'MEF-2022.1' at 7 months.
Figure 7:
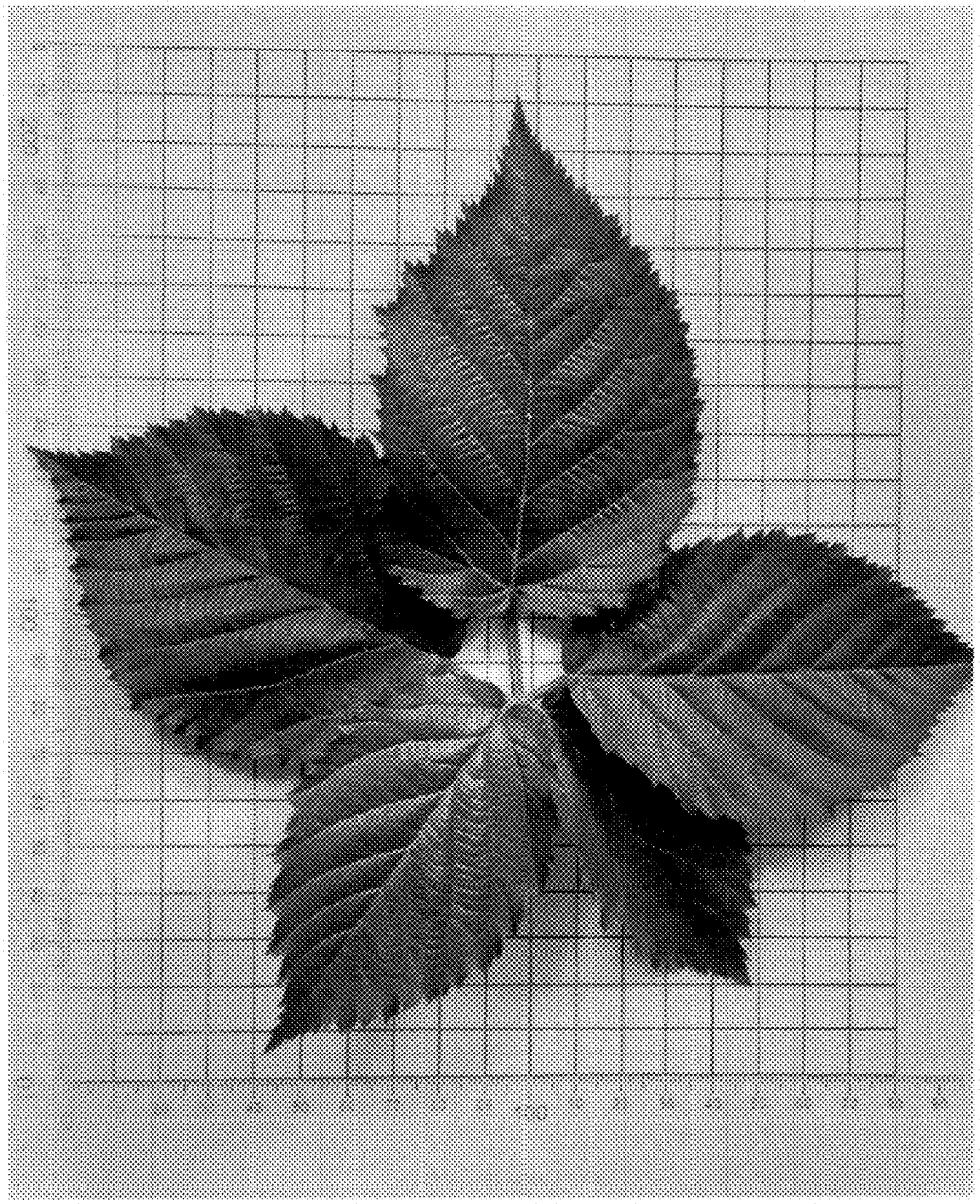
FIG. 7 is a photograph of the adaxial side of a leaf of the new plant 'MEF-2022.1' at 7 months.
Figure 8:
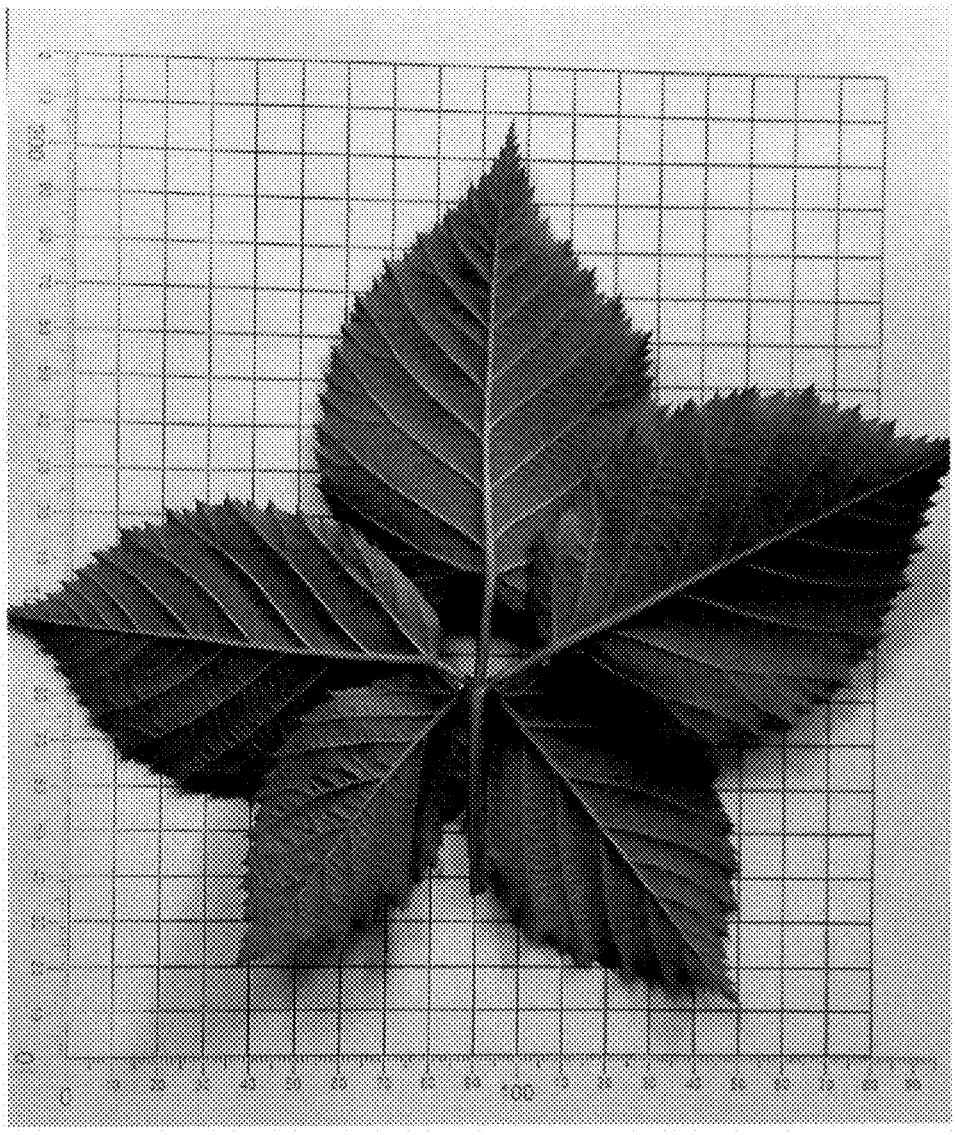
FIG. 8 is a photograph of the abaxial side of a leaf of the new plant 'MEF-2022.1' at 7 months.
Figure 9:
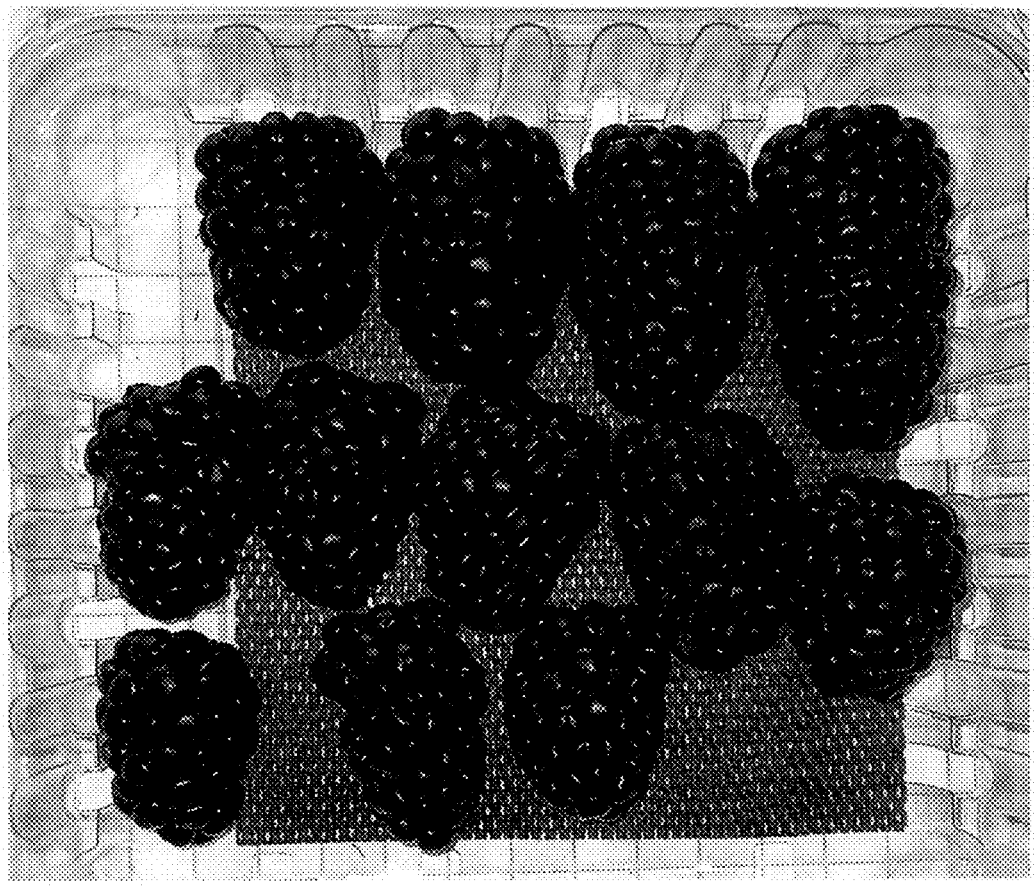
FIG. 9 is a photograph of the ripe fruits of the new plant 'MEF-2022.1' at 7 months.

The following detailed description sets forth the distinctive characteristics of 'MEF-2022.1'. The data which defines these characteristics was collected from asexual reproductions of the original selection. Dimensions, sizes, colors, and other characteristics are approximations and averages set forth as accurately as possible. The plant history was taken on plants approximately 1 to 2 years of age, and the descriptions relate to plants grown in Chimaltenango and Sacatepéquez, Guatemala. Color notations are in reference to hexadecimal color values known to those of ordinary skill in internet website design.

Type: Herbaceous tap-rooted annual.

Classification:

a. *Family*.—Rosaceae.
b. *Genus*.—*Rubus* L. subgenus *Rubus*.
c. *Common name*.—Blackberry.

Parentage:

a. *Female parent*.—Unknown.
b. *Male parent*.—Unknown

Market class: Fresh fruit and food industry.

PLANT

General:

a. *Origin*.—
b. *Size*.—i. Width — 1-1.10 meters. ii. Height — 2-2.5 meters.
c. *Growth habit*.—Upright.
d. *Growth rate*.—i. Time of bud burst — Early, typically April. ii. First emergence of primocanes — Early, typically May.
e. *Guttation*.—Strong.
f. *Propagation*.—Tissue culture, root cuttings and root sowing.
g. *Fertilizer requirement*.—Low nitrogen fertilizers.
h. *Vigor*.—Very Vigorous.

PRODUCTIVITY

General: Very high, about 20 Ton/Ha.

CANES

General: Thornless, erect.

a. *Number of lateral branches*.—5-7.
b. *Lateral branching after tipping* (*measured at the end of growing season*).—7-10.

Floricane:

a. *Cane*.—a. Base Diameter — 10.7 mm. b. Midpoint Diameter — 9.6 mm. c. Terminal Diameter — 7.4 mm.
b. *Color*.—a. Base — #5E3B3B. b. Midpoint — #A14E4C. c. Terminus — #83332E.
c. *Glandular hairs on young shoots*.—None.
d. *Dormant cane shape* (*cross section*).—Angular.
e. *Internode length*.—a. Base — 4.3-4.8 cm. b. Midpoint — 3.4-3.6 cm. c. Terminus — 3-3.6 cm.

Primocane:

a. *Cane*.—a. Base Diameter — 10.7 mm. b. Midpoint Diameter — 9.6 mm. c. Terminal Diameter — 7.4 mm.
b. *Internode length*.—a. Base — 4.3-4.8 cm. b. Midpoint — 3.4-3.6 cm. c. Terminus — 3 -3.6 cm.
c. *Color*.—a. Base — #5E3B3B. b. Midpoint — #A14E4C. c. Terminus — #6E5B0E.
d. *Thorn density*.—None.
e. *Glandular hairs on young shoots*.—None.
f. *Cane shape* (*cross section*).—Angular.

FOLIAGE

General: Abundant, large leaves.

Primocane:

a. *Average date of leaf bud burst*.—7-7.5 months after planting.
b. *Average number of primocane produced each growing season*.—5-8.

Leaves:

a. *Type*.—Pinnately compound.
b. *Size*.—207.0 mm in length including the petiole.
c. *Width*.—227.5 mm.
d. *Length*.—142.5 mm.
e. *Overall shape*.—Ovate.
f. *Glossiness*.—i. Abaxial — Smooth. ii. Adaxial — Glossy.
g. *Color*.—i. Base adaxial — #0E600E. ii. Base abaxial — #4F733F. iii. Midpoint adaxial — #3E5C29. iv. Midpoint abaxial— #3D4E22. v. Terminal adaxial— #324B26. vi. Terminal abaxial— #4B5D31.
h. *Terminal leaflet*.—i. Width — 80.9 mm. ii. Length — 58.4 mm. iii. Shape — Rhombic to obovate. iv. Margin serration — Deeply serrated. 1. Serration teeth length — 1.7-2.5 mm. 2. Serration teeth width — 1-1.5 mm. v. Apex shape — Apiculated. vi. Base shape — Oval.
i. *Number of leaflets per compound leaf*.—3-5.
j. *Venation*.—Parallel.

k. *Young leaf adaxial vein color.*—#697A45.
l. *Young leaf abaxial vein color.*—#82AD6B.
m. *Lobing.*—Broadly lobing.
n. *Shape in cross section.*—Flat.
o. *Degree of blistering between veins.*—Low to medium.
p. *Degree of undulation at margin.*—Very low to low.
q. *Petioles.*—i. Length — 15-62 mm. ii. Color — 1. Adaxial — #BF9278. 2. Abaxial — #AA7177. iii. Diameter — 1.5-3.6 mm. iv. Texture — Smooth.
r. *Petiolules.*—i. Length — 0.9-1.5 mm. ii. Diameter — 0.9-1.5 mm. iii. Color — 1. Adaxial — #CDE99C. 2. Abaxial — #748C3E. iv. Texture — Glossy upper surface, smooth lower surface.
s. *Stipules.*—i. Length — 6.5-11.3 mm. ii. Width — 0.9-1.1 mm. iii. Color — 1. Adaxial — #547424. 2. Abaxial — #7FA55E. iv. Texture — Smooth on both surfaces. v. Shape — Linear.
t. *Rachis.*—i. Length — 22 mm. ii. Diameter — 5 mm. iii. Texture — Smooth. iv. Color — #FDFOEE.

Floricane:

a. *Leaves.*—i. Length — 142.5 mm. ii. Width — 227.5 mm. iii. Overall Shape — Ovate. iv. Average date of leaf bud burst — 3-5 months after planting.
b. *Glossiness.*—Glossy upper surface; smooth lower surface.
c. *Color.*—i. Base adaxial — #0E600E. ii. Base abaxial — #4F733F. iii. Midpoint adaxial — #3E5C29. iv. Midpoint abaxial — #3D4E22. v. Terminal adaxial — #324B26. vi. Terminal abaxial — #4B5D31.
d. *Terminal leaflet.*—i. Width — 80.9 mm. ii. Length — 58.4 mm. iii. Apex shape — Apiculated. iv. Base shape — Oval. v. Shape — Rhombic to obovate. vi. Margin — Serrated. vii. Serration teeth length — 1.7-2.5 mm. viii. Serration teeth width — 1-1.5 mm. ix. Number of leaflets per compound leaf — 3-5. x. Lobing — Broadly lobing. xi. Shape in cross section — Angular.
e. *Degree of blistering between veins.*—Absent to weak.
f. *Degree of undulation at margin.*—Very low to low.
g. *Petioles.*—i. Length — 15-62 mm. ii. Diameter — 1.5 — 3.6 mm. iii. Color — 1. Adaxial side — #BF9278. 2. Abaxial surface — #AA7177. iv. Texture — Smooth.
h. *Petiolules.*—i. Length — 0.9-1.5 mm. ii. Diameter — 0.9-1.5 mm. iii. Color — 1. Adaxial side — #CDE99C. 2. Abaxial surface — #748C3E. iv. Texture — Smooth.
i. *Stipules.*—i. Length — 6.5-11.3 mm. ii. Width — 0.9 -1.1 mm. iii. Texture — Glossy upper surface, smooth lower surface. iv. Shape — Linear. v. Color — 1. Adaxial — #547424. 2. Abaxial — #7FA55E.

FLOWERS

Floricane:

a. *Date of bloom.*—80-150 days after planting; typically June.
b. *Reproductive organs.*—i. Stamens — 80-150. 1. Color — #fcfcfc. ii. Pistils — 80-120. iii. Pollen — Abundant. 1. Color — #f2c230. iv. Style — 1. Length — 0.35 cm. 2. Color — #fff7de. v. Ovary — 1. Color — #fff7de.
c. *Flower.*—i. Diameter — 15 mm-30 mm. ii. Depth — 0.5-1.5 mm. iii. Shape — Rotate. iv. Symmetry — Actinomorphic. v. Fragrance — None.
d. *Petals.*—i. Number per flower — 5 per flowering point. ii. Length — 10-15 mm. iii. Width — 12-15 mm. iv. Shape — Rhombic to obovate. v. Apex — Acute. vi. Margin — Smooth. vii. Base — Acute. viii. Color — 1. Adaxial surface — #FFFFFF. 2. Abaxial surface — #CAC3C2. ix. Texture — 1. Adaxial — Smooth. 2. Abaxial — Smooth.
e. *Flower bud.*—i. Flowers per cluster — 5-8. ii. Length — 18 mm. iii. Width — 7 mm. iv. Color — 1. Adaxial — #.2FD307 2. Abaxial — #.9BD305
f. *Sepal.*—i. Number per flower — 5. ii. Length — 5-6.5 mm. iii. Width — 4-5 mm. iv. Shape — Rhombic to obovate. v. Apex — Acuminate. vi. Margin — Smooth. vii. Base —Fused. viii. Texture — Smooth on the upper and lower surfaces. ix. Color — 1. Adaxial — #60872A. 2. Abaxial — #364315.
g. *Pedicel.*—i. Length — 50-80 mm. ii. Width — 1.3-1.5 mm. iii. Color — #48522F. iv. Texture — Smooth.
h. *Peduncle.*—i. Length — 50-90 mm. ii. Width — 1.3-1.5 mm. iii. Color — #48522F. iv. Texture — Smooth.
i. *Cyme.*—i. Length — 100-190 mm. ii. Width — 2.5-4.0 mm. iii. Color — #48522F.

FRUIT

General:

a. *Maturity.*—i. Average first ripe date — 1 month after flowering; August. ii. Average fruiting period — 3 months; August-October.
b. *Size.*—i. Length — 30-33 mm.
c. *Shape.*—Elongated.
d. *Weight.*—13-16 grams.
e. *Firmness.*—Hard.
f. *Texture.*—Smooth.
g. *Color.*—#240606.
h. *Diameter of fruit at primary position on inflorescence.*—20-23 mm.
i. *Diameter of fruit at secondary positions on inflorescence.*—16-19 mm.
j. *Drupelet size.*—i. Length — 6 mm. ii. Width — 5 mm.
k. *Drupelet number per fruit.*—80-135.
l. *Seed.*—i. Length — 3-4 mm. ii. Width — 2-2.4 mm. iii. Wet weight — 5-6 mg. iv. Color wet — #944304. v. Color dry — #866E4C.
m. *Soluble solids.*—15.1° Bx.
n. *PH.*—3.10.
o. *Titratable acidity.*—1.01%
p. *Uses.*—Fresh food and food industry.
q. *Disease resistance/susceptibility.*—Susceptibility to Anthracnose, Resistance to powdery mildew and downy mildew (*Peronospora sparsa*).
e. *Fruiting lateral.*—i. Typical and observed fruiting lateral length — 2 meters. ii. Typical and observed fruiting lateral diameter — 12 mm. iii. Texture — Pubescent. iv. Number of fruits per lateral — 15-17 fruits per lateral. v. Time of emergence (month) — August. vi. Color — #44BC4F.

The invention claimed is:

1. A new and distinct variety of blackberry plant named 'MEF-2022.1', as illustrated and described herein.

* * * * *